United States Patent [19]

Akao et al.

[11] Patent Number: 4,844,787
[45] Date of Patent: Jul. 4, 1989

[54] PACKAGING BAG FOR SHEETS FOR ELECTROPHORESIS

[75] Inventors: Mutsuo Akao, Kanagawa; Takeshi Kato, Saitama, both of Japan

[73] Assignee: Fuji Photo Film Co., Ltd., Kanagawa, Japan

[21] Appl. No.: 100,769

[22] Filed: Sep. 24, 1987

[30] Foreign Application Priority Data

Sep. 26, 1986 [JP] Japan .................. 61-226279

[51] Int. Cl.⁴ .......................................... G01N 27/28
[52] U.S. Cl. .............................. 204/299 R; 204/182.8; 204/180.1
[58] Field of Search ............. 204/299 R, 182.8, 180.1; 428/35

[56] References Cited

U.S. PATENT DOCUMENTS 3,975,162  8/1976  Renn ................................ 436/169
4,322,480  3/1982  Tuller et al. ..................... 428/476.1

Primary Examiner—John F. Niebling
Assistant Examiner—John S. Starsiak, Jr.
Attorney, Agent, or Firm—Jules E. Goldberg

[57] ABSTRACT

A packaging bag for a sheet for electrophoresis comprising a polyethylene resin layer containing more than 50 wt. % of polyethylene resin having a density of 0.935 to 0.970 g/cm³ and a melt index of 0.1 to 1.5 g/10 minutes, the thickness of said polyethylene resin layer is 70 to 200 μm, and haze of said bag is 15 to 95%.

This packaging bag is excellent is moistureproofness capable of preserving the sheets for electrophoresis without deterioration of quality, and the sheets for electrophoresis can be inspected from the outside. This packaging bag has not the problem as the packaging material for the sheet for electrophoresis such as curling, insertion nor blocking, and it is inexpensive.

4 Claims, 2 Drawing Sheets

PACKAGING BAG FOR SHEETS FOR ELECTROPHORESIS

BACKGROUND OF THE INVENTION

1. Field of the Invention

This invention relates to a packaging bag for the sheet for electrophoresis composed of a gel membrane for electrophoresis and two sheets of the support supporting the gel membrane from both sides.

2. Description of Prior Art

The electrophoretic operation is known to separate charged molecules or particles such as proteins, their hydrolyzates, nucleic acids and their hydrolyzates by utilizing the phenomenon that they migrate in a sheet medium such as gel membrane or filter paper impregnated with a pH buffer by loading an electric filed. This electrophoretic operation is utilized for the separation and identification of the above biopolymers and the like.

Besides, in the field of genetic engineering, electrophoretic operation is used, for example, in order to determine the base sequence of nucleic acid such as DNA by utilizing autoradiography. In general, the electrophoretic operation for this purpose contains the operation where two or more kinds of base-specific reacting species of DNA or DNA fragments labeled with radioisotope are allowed to migrate in parallel along the direction of the electric field of the medium for electrophoresis. The electrophoretic patterns obtained as autoradiogram (the aggregate of zones formed on the medium by the electrophoresis) are compared with each other to determine the base sequence. This comparison utilizes the principle of the electrophoresis that the base-specific reacting species having the same molecular weight migrate to the same position when their starting points are the same.

The medium for electrophoresis is usually filter paper, membrane filter, starch gel membrane, polyacrylamide gel membrane or the like, and it is a sheet having an uniform thickness. In the past, the gel membrane such as starch gel membrane or polyacrylamide gel membrane was prepared by pouring the solution for forming gel membrane into the frame put on a support made of a nonconductive material such as glass plate. Then, another support plate was put thereon, and allowed to stand to form the gel membrane. However, this preparation work was troublesome, and moreover, the gel membrane was sometimes damaged at the time of removing the glass plate prior to the operation of autoradiography.

As the means of solving these problems, a gel membrane hard to be damaged has been disclosed (Japanese Patent KOKAI No. 59-126236). Besides, an easily usable sheet for electrophoresis (Japanese Patent KOKAI No. 59-126237) and its preparation method (Japanese Patent KOKAI No. 60-203847) have also been disclosed. This sheet for electrophoretsis is, as shown in FIG. 12, composed of two gel membrane support sheets 12, 12 disposed at a prescribed interval through a spacer 13 and a gel membrane for electrophoresis 14 formed between the support sheets 12,12. The support sheets are made of nonconductive organic polymer film. As shown in FIG. 7, a slot 11 is provided over the whole upper edge of the gel membrane 14, and many recesses 15 for receiving samples are formed in a row at its bottom. Such an electrophoretic sheet has been developed for mass production, and accordingly it is necessary to be protected so as not to deteriorate its quality during storage. While, the polyacrylamide solution for the preparation of polyacrylamide gel membrane contains 63 grams of urea in 150 ml of the solution. The preparation method of polyacrylamide gel membrane for electrophoresis is described in "Manual of DNA Sequence Analysis" (Ed. by M. Takanami et al, p 49 -, Kodansha, Japan). This content is near the saturation of urea. Therefore, when water evaporates from the polyacrylamide gel membrane, urea in the gel deposits in a short time. The deposition occurs particularly at the part of the slot. Thus, it is necessary to prevent the water evaporation during storage.

The present inventor has investigated in order to obtain a suitable packaging material for the gel membrane for electrophoresis capable of preserving without the deterioration of quality. For example, the packaging material of FIG. 9 is composed of high-pressure branched low-density polyethylene (LDPE) resin layer 7 having a thickness of 100 $\mu$m or 200 $\mu$m. The packaging bag made of this packaging material was not suitable for the gel membrane for electrophoresis, because urea deposited during the storage within one year. The packaging material of FIG. 10 is composed of a thermoplastic resin layer 2, an aluminum foil layer 8 laminated thereon through an adhesive layer 3, and a paper layer 9 further laminated thereon through an adhesive layer 3. Using this packaging material, the bag 4 shown in FIG. 11 was made. All side edges 10 of this bag 4 were heat-sealed. The moistureproofness of this bag is good, but the gel membrane in the bag cannot be inspected because of invisibility. When the bag was opened by a scissors, the gel membrane was occasionally cut together with the bag because its inside could not be seen. The curling of this packaging material was large, and the insertion of the gel membrane was bad. The blocking of the packaging material was also a problem, and moreover, it was expensive.

SUMMARY OF THE INVENTION

An object of the invention is to provide a packaging bag for sheets for electrophoresis excellent in moistureproofness capable of preserving the sheets for electrophoresis without deterioration of quality.

Another object of the invention is to provide a packaging bag for sheets for electrophoresis capable of inspecting the sheets from the outside.

Another object of the invention is to provide a packaging bag for sheets for electrophoresis not having the problem as the packaging material for the sheets such as curling, insertion nor blocking.

Still another object of the invention is provide a packaging bag for sheets for electrophoresis which is inexpensive.

The present invention provides a packaging bag containing sheets for electrophoresis which has achieved these objects. Such a packaging bag comprises a polyethylene resin layer containing more than 50 wt.% of polyethylene resin having a density of 0.935 to 0.970 g/cm$^3$ and a melt index of 0.1 to 1.5 g/10 minutes, the thickness of said polyethylene resin layer is 70 to 200 $\mu$m, and haze of said bag is 15 to 95%.

DETAILED DESCRIPTION OF THE INVENTION

Figure 1:
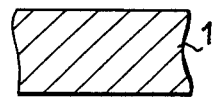
FIGS. 1 to 6 are partial sectional views of the packaging bags embodying the invention.

The polyethylene resin composing the polyethylene resin layer has a density of 0.935 to 0.970 g/cm$^3$ and a melt index (MI) of 0.1 to 1.5 g/10 minutes. When the density is lower than 0.935 g/cm$^3$, moistureproofness becomes insufficient because of low crystallinity. The insertion of products becomes bad, and the film made of this resin is easily deformed by loading a tension. While, when the density is higher than 0.970 g/cm$^3$, crystallinity becomes too high. Molecular orientation easily occurs in the longitudinal direction, and the film made of this resin is easily torn. Transparency becomes bad, and the moldability of inflation film and heat sealability are also bad. On the other hand, when MI is lower than 0.1 g/10 minutes, the moldability of the inflation film having a thickness of thicker than 70 μm becomes bad. While, when MI is higher than 1.5 g/10 minutes, moistureproofness becomes insufficient because molecular weight is small. Bag-making aptitude and the insertion of the sheets for electrophoresis have also problems.

The polyethylene resin layer contains more than 50 wt.% of the above polyethylene resin. That is, the resin of this layer may be composed of the above polyethylene resin alone. When another resin is blended with this resin, the resin for blending may be selected from LDPE resin, mediumdensity, polyethylene resin, low-pressure linear low-density polyethylene resin, ethylene-ethyl acrylate copolymer (EEA) resin, ethylene-vinyl acetate copolymer (EVA) resin, ionomer resin or the like. When the content of the above polyethylene resin is less than 50 wt.% moistureproofness becomes insufficient. The sealability by heat-sealing becomes bad. The thickness of the polyethylene resin layer is 70 to 200 μm. When the thickness is thinner than 70 μm, moistureproofness becomes insufficient. While, when the thickness is thicker than 200 μm, film moldability becomes a problem. The inspection of the sheets for electrophoresis from the outside becomes also difficult.

The packaging bag for the sheets for electrophoresis may be either a single layer film of the polyethylene resin layer or a coextruded multilayer film. This coextruded film is composed of two or more layers of the polyethylene resin layers or a combination of the polyethylene resin layer(s) and other thermoplastic resin layer(s) such as other polyethylene resin layer(s) or other polyolefin resin layer(s). However, the haze of the packaging bag should be 15 to 95% as the whole. The measuring method of haze is according to ASTM D-1003. When the haze is beyond 95%, the inspection of the sheet becomes difficult. Moreover, the tensile yield strength (JIS K-6760, ASTM D-638) is preferably stronger than 170 kg f/cm$^2$ in order to prevent the elongation of the film by the tension at winding up, to impart automatic bag-making aptitude, and to prevent the separation of heat-sealed part. The bending rigidity (flexural stiffness) (JIS-K-7106, ASTM D-747) is also preferably stronger than 5000 kg f/cm$^2$ in order to make the insertion of the sheet for electrophoresis well and to protect the sheet.

Various additives may be blended in order to secure the above properties or for other purposes. Such an additive includes organic or inorganic nucleating agent and inorganic white pigment.

Partial sections of the packaging bags embodying the invention are illustrated in FIG. 1 to 6.

The packaging bag of FIG. 1 is composed of the polyethylene resin layer 1.

Figure 2:
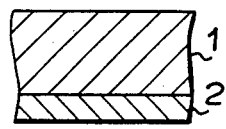

The packaging bag of FIG. 2 is composed of a coextruded double layer film consisting of the polyethylene resin layer 1 and a thermoplastic resin layer 2.

Figure 3:
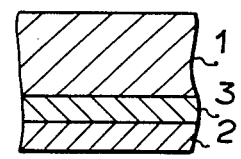

The packaging bag of FIG. 3 is composed of a coextruded triple layer film consisting of the polyethylene resin layer 1, an adhesive layer 3 and a thermoplastic resin layer 2.

Figure 4:
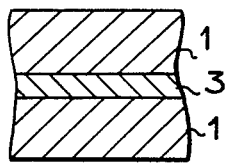

The packaging bag of FIG. 4 is composed of a coextruded triple layer film consisting of the polyethylene resin layer 1, an adhesive layer 3 and the polyethylene resin layer 1.

Figure 5:
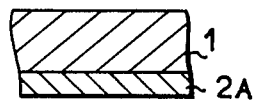

The packaging bag of FIG. 5 is composed of a coextruded double layer film consisting of the polyethylene resin layer 1 and a low temperature heat seal layer 2A composed of EEA resin, EVA resin ionomer resin or the like.

Figure 6:
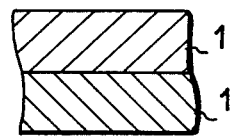

The packaging bag of FIG. 6 is composed of a coextruded double layer film consisting of two layers of the polyethylene resin layers 1,1.

Figure 7:
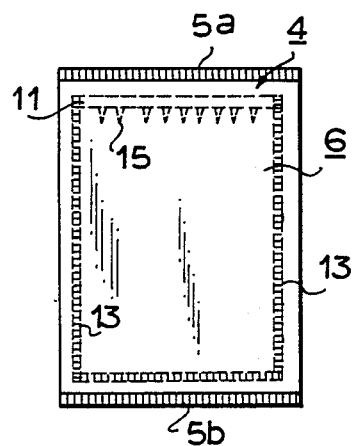
FIG. 7 is a plan view thereof.
Figure 8:
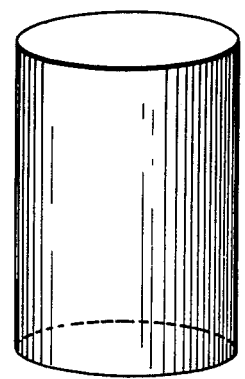
FIG. 8 is a perspective view of an inflation film cut into a prescribed length.

A form of the packaging bag of the invention is shown in FIG. 7. The film composing the packaging bag is molded by inflation process. The endless tube of the inflation film is cut into a prescribed length as shown in FIG. 8, and its lower end 5b is heat-sealed. The sheet for electrophoresis 6 is inserted in it, and then, its upper end 5a is heat-sealed.

Figure 11:
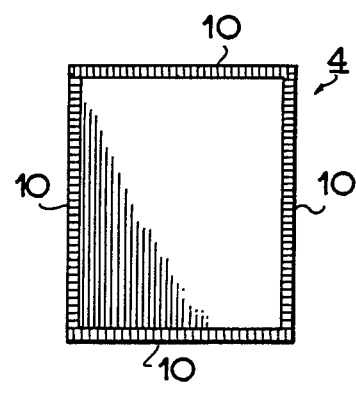
FIG. 11 is a plan view of the packaging bag of which all side edges were heat-sealed.
Figure 12:
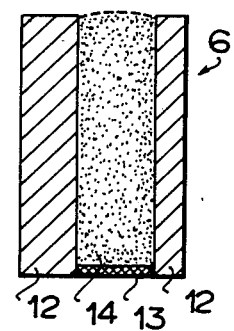
FIG. 12 is a partial sectional view of a sheet for electrophoresis.

Another form of the packaging bag of the invention is shown in FIG. 11.

EXAMPLES

The packaging bag of Example 1 corresponds to the embodiment of FIG. 1. The polyethylene resin layer 1 is made of the high-density polyethylene (HDPE) having a density of 0.950 g/cm$^3$ and a MI of 0.6 g/10 minutes. Its thickness is 100 μm, and its haze is 62%.

The packaging bag of Example 2 also corresponds to the embodiment of FIG. 1. The polyethylene resin layer 1 is made of the HDPE having a density of 0.950 g/cm$^3$ and a MI of 0.6 g/10 minutes. Its thickness is 150 μm, and its haze is 78%.

The packaging bag of Example 3 correspond to the embodiment of FIG. 2. The polyethylene resin layer 1 is made of the HDPE having a density of 0.950 g/cm$^3$ and MI of 0.6 g/10 minutes. Its thickness is 80 μm. The thermoplastic resin layer 2 is made of the LDPE having a density of 0.923 g/cm$^3$ and a MI of 0.9 g/10 minutes. Its thickness is 60 μm. The haze of this film is 57%.

Figure 9:
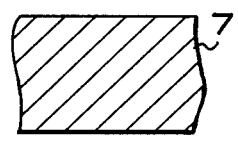
FIG. 9 and 10 are partial sectional views of comparative products.

Comparative packaging bag 1 corresponds to the embodiment of FIG. 9. The thermoplastic resin layer 2 is made of the LDPE having a density of 0.923 g/cm$^3$ and a MI of 0.9 g/10 minutes. Its thickness is 100 μm, and its haze is 6%.

Figure 10:
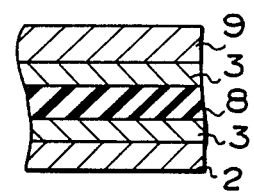

Comparative packaging bag 2 corresponds to the embodiment of FIG. 10. This bag is made of the laminated film consisting of 40 μm in thickness of paper 9, 15 μm of polyethylene resin adhesive layer 3, 7 μm of aluminum foil 8, 15 μm of polyethylene resin adhesive layer 3, and 50 μm of LDPE resin thermoplastic resin layer 2. Its haze is 100%.

Comparative packaging bag 3 corresponds to the embodiment of FIG. 9. The thermoplastic resin layer 2 is made of the LDPE having a density of 0.923 g/cm³ and a MI of 0.9 g/10 minutes. Its thickness is 200 μm, and it haze is 13%.

The constitutions of these bags are tablated in Table 1.

Various properties of these bags were measured, and the results are shown in Table 2.

TABLE 1

|  | INVENTION | | | COMPARATIVE | | |
|---|---|---|---|---|---|---|
|  | 1 | 2 | 3 | 1 | 2 | 3 |
| Embodiment Production of Film | FIG. 1 Monolayer Inflation | FIG. 1 Monolayer Inflation | FIG. 2 Double Layer Coextruded Inflation | FIG. 9 Monolayer Inflation | FIG. 10 Laminated | FIG. 9 Monolayer Inflation |
| Layer Material | HDPE 100 μm D*¹: 0.950 MI: 0.6 | HDPE 150 μm D: 0.950 MI: 0.6 | HDPE 80 μm D: 0.950 MI: 0.6 LDPE 60 μm D: 0.923 MI: 0.9 | LDPE 100 μm D: 0.923 MI: 0.9 | Paper 40 μm PE Ad*² 15 μm Al 7 μm PE Ad 15 μm LDPE 50 μm | LDPE 200 μm D: 0.923 MI: 0.9 |
| Form of Bag | FIG. 7 | FIG. 7 | FIG. 7 | FIG. 7 | FIG. 11 | FIG. 7 |

*¹Density
*²Adhesive layer

TABLE 2

|  | INVENTION | | | COMPARATIVE | | | Test Method |
|---|---|---|---|---|---|---|---|
|  | 1 | 2 | 3 | 1 | 2 | 3 |  |
| Visibility*¹ | B | B | B | A | E | A | I |
| Judgement on Troubles of Product in Bag | B | B | B | A | E | B | II |
| Curling | B | B | B | B | E | B | III |
| Insertion | A | A | B | D | C | B | IV |
| Moisture-proofness | B | B | B | E | B | E | V |
| Evaporation (g) | 0.21 | 0.13 | 0.20 | 0.55 | 0.11 | 0.25 | VI |
| Haze (%) | 62 | 78 | 57 | 6 | 100 | 13 | VII |

*Visibility of a sheet for electrophoresis

The evaluations in the table were carried out as follows:
A very excellent; B excellent;
C practical; D having a problem;
E impractical.
Test Method I: Visual inspection Test Method II: Judged by the degree capable of visually inspecting the troubles such as foams of the sheet for electrophoresis packaged in each bag.

Test Method III: Judged by the insertion of the sheet for electrophoresis from the upper side opening of the bag of FIG. 7 or FIG. 11.

Test Method IV: Judged by the insertion of the sheet for electrophoresis from the upper side opening of the bag of FIG. 7 or FIG. 11.

Test Method V: JIS Z 0208-1976

Test Method VI: A sheet for electrophoresis was sealed in the packaging bag of FIG. 7 having a size of 20 cm×40 cm, and warmed at 50° C. for 20 hours. The evaporation amount of water per one sheet for electrophoresis was then measured.

Test Method VII: ASTM D-1003

We claim:

1. A packaging bag containing at least one sheet for electrophoresis, said bag comprising a polyethylene resin layer consisting essentially of 50 wt.% of polyethylene resin having a density of 0.935 to 0.970 g/cm³ and a melt index of 0.1 to 1.5 g/10 minutes, the thickness of said polyethylene resin layer being 70 to 200 μm, and haze of said bag being 15 to 95%.

2. The packaging bag of claim 1 having a tensile yield strength greater than 170 kg f/cm².

3. The packaging bag of claim having a bending rigidity greater than 5,000 kg f/cm².

4. The packaging bag of claim 1 wherein said sheet for electrophoresis is a gel membrane containing a material in a concentration near to its saturation concentration.

* * * * *